United States Patent
Park et al.

(10) Patent No.: US 10,222,354 B2
(45) Date of Patent: Mar. 5, 2019

(54) NON-CONTACT DURABILITY DIAGNOSIS APPARATUS AND METHOD

(71) Applicants: Kia Motors Corporation, Seoul (KR); Korea Advanced Institute of Science and Technology, Daejeon (KR)

(72) Inventors: Jae Roung Park, Gyeonggi-do (KR); Cheol Woo Lim, Gyeonggi-do (KR); Byeong-Jin Park, Daejeon (KR); Byeongju Song, Daejeon (KR); Hoon Sohn, Daejeon (KR)

(73) Assignees: Kia Motors Corporation, Seoul (KR); Korea Advanced Institute of Science and Technology, Daejeon (KR)

( * ) Notice: Subject to any disclaimer, the term of this patent is extended or adjusted under 35 U.S.C. 154(b) by 422 days.

(21) Appl. No.: 14/955,910

(22) Filed: Dec. 1, 2015

(65) Prior Publication Data

US 2017/0023530 A1 Jan. 26, 2017

(30) Foreign Application Priority Data

Jul. 22, 2015 (KR) .................. 10-2015-0103773

(51) Int. Cl.
*G01N 29/44* (2006.01)
*G01N 29/12* (2006.01)

(52) U.S. Cl.
CPC ......... *G01N 29/12* (2013.01); *G01N 29/4463* (2013.01); *G01N 2291/0258* (2013.01); *G01N 2291/2623* (2013.01); *G01N 2291/2626* (2013.01)

(58) Field of Classification Search
CPC ............... G01N 29/12; G01N 29/4463; G01N 2291/0258; G01N 2291/2623; G01N 2291/2626
See application file for complete search history.

(56) References Cited

U.S. PATENT DOCUMENTS 5,369,998 A * 12/1994 Sowerby .................. G01F 1/66
73/861.04
5,977,538 A * 11/1999 Unger .................. A61B 5/0091
250/227.2

(Continued)

FOREIGN PATENT DOCUMENTS

JP 2002022714 A * 1/2002
JP 2013-156277 A 8/2013

(Continued)

*Primary Examiner* — Natalie Huls
(74) *Attorney, Agent, or Firm* — Mintz Levin Cohn Ferris Glovsky and Popeo, P.C.; Peter F. Corless (57) ABSTRACT

A non-contact durability diagnosis apparatus includes: (a) applying non-contactly and sequentially at least two excitation ultrasonic waves to an object and storing frequency signals generated from the object; (b) applying non-contactly and simultaneously the at least two excitation ultrasonic waves to the object and storing frequency signals generated from the object; (c) storing derived frequency signals remaining after removing an overlapping portion of the frequency signals of step (a) and the frequency signals of step (b); and (d) determining that the object is damaged when at least one of the generated frequency signals of step (c) is larger than a predetermined value.

10 Claims, 8 Drawing Sheets

(56) References Cited

U.S. PATENT DOCUMENTS

| | | | | |
|---|---|---|---|---|
| 6,047,602 | A * | 4/2000 | Lynnworth | G01F 1/662 73/632 |
| 2004/0134970 | A1* | 7/2004 | Den Boer | B23K 31/12 228/104 |
| 2008/0059114 | A1* | 3/2008 | Coperet | G01B 17/02 702/171 |
| 2012/0240681 | A1* | 9/2012 | Lopez Jauregui | G01N 29/043 73/643 |
| 2012/0310064 | A1* | 12/2012 | McGee | A61B 8/0883 600/373 |
| 2013/0102865 | A1* | 4/2013 | Mandelis | A61B 5/0095 600/328 |
| 2013/0167644 | A1* | 7/2013 | Deschamps | G01N 29/043 73/587 |
| 2014/0224021 | A1* | 8/2014 | Edwards | A61B 5/0048 73/601 |
| 2015/0265158 | A1* | 9/2015 | Edwards | G01N 22/00 600/407 |
| 2016/0113625 | A1* | 4/2016 | Kim | G01N 29/221 600/459 |
| 2017/0146492 | A1* | 5/2017 | Luo | G01N 29/223 |
| 2017/0332909 | A1* | 11/2017 | Nagae | A61B 5/0035 |

FOREIGN PATENT DOCUMENTS

| | | |
|---|---|---|
| KR | 10-2009-0094447 A | 9/2009 |
| KR | 10-2010-0092233 A | 8/2010 |
| KR | 10-2012-0090170 A | 8/2012 |

\* cited by examiner

NON-CONTACT DURABILITY DIAGNOSIS APPARATUS AND METHOD

CROSS-REFERENCE TO RELATED APPLICATION

The present application claims priority to and the benefit of Korean Patent Application Number 10-2015-0103773 filed on Jul. 22, 2015, the entire contents of which are incorporated herein for all purposes by reference.

BACKGROUND OF DISCLOSURE (a) Field of Disclosure

The present disclosure relates generally to a non-contact durability diagnosis apparatus and control method thereof which non-contactly identify and confirm damage of an object.

(b) Description of Related Art

In general, it's important for an object such as a shaft or a rail, which is used to secure durability, to be checked for damage, such as the presence of a crack. Damage of such objects can be identified using a contact-type vibration sensor or an ultrasonic wave measuring instrument. A contact-type vibration sensor includes, for example, a drive motor rotating an object and a vibration sensor detecting damage of the rotating object. The vibration sensor can confirm whether the object is damaged while the object is being rotated.

Because the contact-type vibration sensor confirms whether an object is damage while the object is rotating, the damage cannot be identified in advance of an abnormality being generated. In addition, an ultrasonic wave measuring instrument identifies damage of an object while it is rotated using a drive motor.

However, ultrasonic wave measuring instrument has a problem that excessive measurement noises occur during a measurement process, which uses ultrasonic waves, and thus fails to correctly identify damage of an object.

The above information disclosed in this Background section is only for enhancement of understanding of the background of the disclosure, and therefore, it may contain information that does not form the related art that is already known in this country to a person of ordinary skill in the art.

SUMMARY OF DISCLOSURE

Various aspects of the present disclosure are directed to providing non-contact durability diagnosis apparatus and method which non-contactly identify and confirm damage of an object using ultrasonic waves.

According to embodiments of the present disclosure, a non-contact durability diagnosis method includes: (a) applying non-contactly and sequentially at least two excitation ultrasonic waves to an object and storing frequency signals generated from the object; (b) applying non-contactly and simultaneously the at least two excitation ultrasonic waves to the object and storing frequency signals generated from the object; (c) storing derived frequency signals remaining after removing an overlapping portion of the frequency signals of step (a) and the frequency signals of step (b); and (d) determining that the object is damaged when at least one of the generated frequency signals of step (c) is larger than a predetermined value.

Step (a) may include: (a-1) applying sequentially a first excitation ultrasonic wave and a second excitation ultrasonic wave having a frequency different than a frequency of the first excitation ultrasonic wave; and (a-2) measuring and storing a first frequency signal generated from the object by the first excitation ultrasonic wave and a second frequency signal generated from the object by the second excitation ultrasonic wave.

Step (b) may include: (b-1) applying non-contactly and simultaneously the first excitation ultrasonic wave and the second excitation ultrasonic wave to the object; and (b-2) measuring and storing a third frequency signal and a fourth frequency signal generated from the object by the simultaneous application of the first excitation ultrasonic wave and the second excitation ultrasonic wave in step (b-1).

The stored frequency signals in step (c) are derived by removing an overlapping portion of the first frequency signal and the second frequency signal of step (a-2) and the third frequency signal and the fourth frequency signal of step (b-2) step from the third frequency signal and the fourth frequency signal of step (b-2).

The first excitation ultrasonic wave has a frequency lower than that of the second excitation ultrasonic wave.

The method may further include (e) notifying a user of damage information of the object when at least one of the derived frequency signals is greater than a predetermined value.

The method may further include (f) displaying the damage information on a display portion.

Furthermore, according to embodiments of the present disclosure, a non-contact durability diagnosis apparatus includes: a first signal generator non-contactly applying a first excitation ultrasonic wave to an object and generating a first frequency signal from the object; a second signal generator non-contactly applying a second excitation ultrasonic wave different than the first excitation ultrasonic wave to the object and generating a second frequency signal from the object; a first controller controlling the first signal generator and the second signal generator in order to sequentially perform a first step of applying the first excitation ultrasonic wave and the second excitation ultrasonic wave sequentially to the object and a second step of generating synthesized frequency signals from the object by applying the first excitation ultrasonic wave and the second excitation ultrasonic wave simultaneously to the object; a storing portion storing the first frequency signal and the second frequency signal generated from the object by the first step and the synthesized frequency signals generated from the object by the second step; and a second controller identifying frequency signals derived by removing an overlapping portion of the first frequency signal and the second frequency signal, from the synthesized frequency signals, and determining that the object is damaged if at least one of the derived frequency signals is larger than a predetermined range or value.

The first excitation ultrasonic wave has a frequency lower than that of the second excitation ultrasonic wave.

The apparatus may further include a display portion connected to the second controller and displaying damage information of the object.

DETAILED DESCRIPTION OF THE EMBODIMENTS

Reference will now be made in detail to various embodiments of the present disclosure, examples of which are illustrated in the accompanying drawings and described below. While the disclosure will be described in conjunction with embodiments, it will be understood that present description is not intended to limit the disclosure to those embodiments. On the contrary, the disclosure is intended to cover not only the disclosed embodiments, but also various alternatives, modifications, equivalents and other embodiments, which may be included within the spirit and scope of the disclosure as defined by the appended claims.

Parts which are not related to the description are omitted for clearly describing the embodiments of the present disclosure. Like reference numerals refer to like or similar elements throughout the specification. Names of components such as first, second, and the like are merely intended to assign a number to the names because the names of the components are the same as each other, while an order thereof is not particularly limited.

Additionally, it is understood that one or more of the below methods, or aspects thereof, may be executed by at least one control unit. The term "control unit" may refer to a hardware device that includes a memory and a processor. The memory is configured to store program instructions, and the processor is specifically programmed to execute the program instructions to perform one or more processes which are described further below. Moreover, it is understood that the below methods may be executed by an apparatus comprising the control unit in conjunction with one or more other components, as would be appreciated by a person of ordinary skill in the art.

Figure 1:
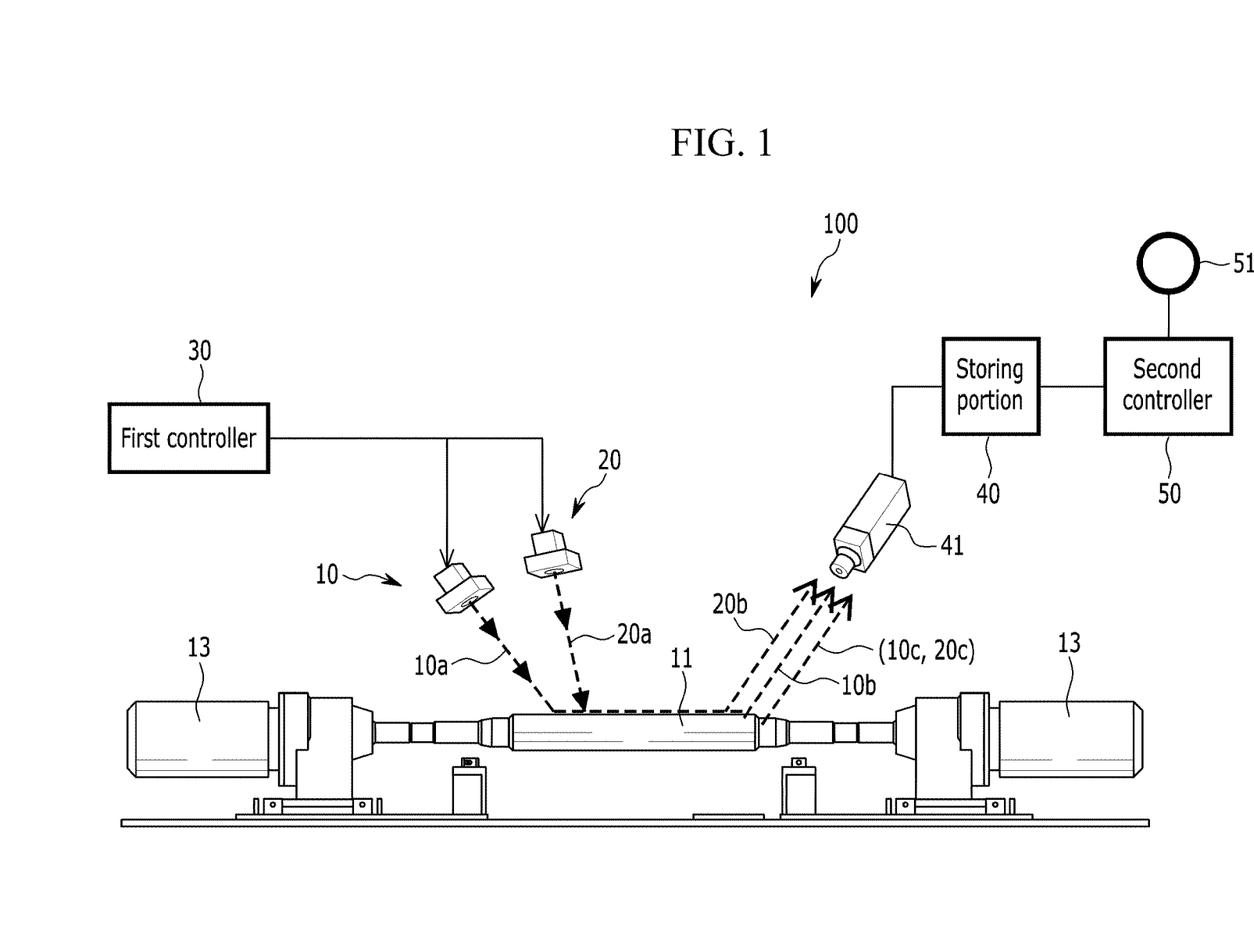
FIG. 1 is a side view illustrating schematically an exemplary non-contact durability diagnosis apparatus according to the present disclosure.
Figure 2:
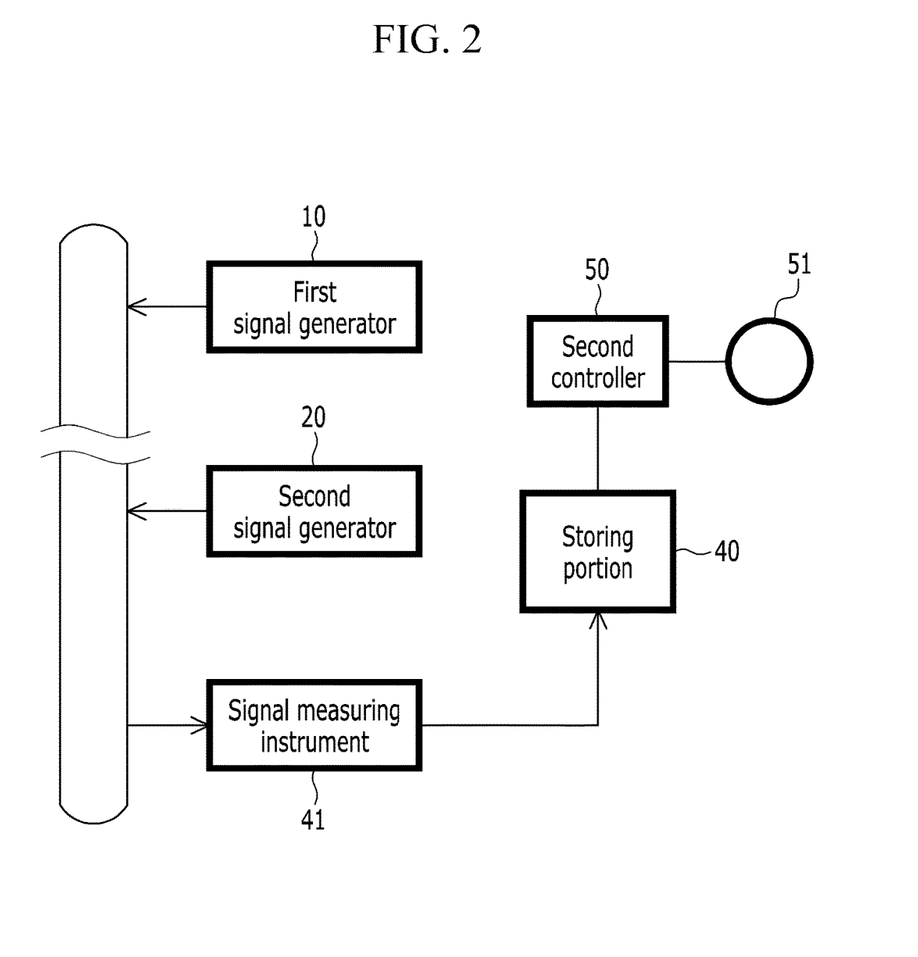
FIG. 2 is a block diagram illustrating schematically the exemplary non-contact durability diagnosis apparatus of FIG. 1.

Referring now to the disclosed embodiments, FIG. 1 is a side view illustrating schematically an exemplary non-contact durability diagnosis apparatus according to the present disclosure. FIG. 2 is a block diagram illustrating schematically the exemplary non-contact durability diagnosis apparatus of FIG. 1.

As shown in FIG. 1 and FIG. 2, an exemplary non-contact durability diagnosis apparatus 100 according to the present disclosure may comprise a first signal generator 10 for non-contactly applying a first excitation ultrasonic wave 10a to an object 11, a second signal generator 20 for non-contactly applying a second excitation ultrasonic wave 20b to the object 11, a first controller 30 controlling the first signal generator 10 and the second signal generator 20 to apply the first excitation ultrasonic wave 10a and the second excitation ultrasonic wave 20a to the object 11, a storing portion 40 respectively storing a first frequency signal 10b and a second frequency signal 20b generated from the object 11 and synthesized frequency signals 10c and 20c, and a second controller 50 identifying derived frequency signals 12 derived by removing an overlapping portion of the first frequency signal 10b and the second frequency signal 20b from the synthesized frequency signal 10c and 20c and confirming the object 11 is damaged if at least one of the derived frequency signals 12 is larger than a predetermined range or value.

An object 11 is a component such as a shaft or a rail, which is utilized to secure durability. The object 11 is not limited to a shaft or a rail, however, and may be any component which secures durability greater than a predetermined strength.

The object 11 may be fixed to a mounting place by fixing means 13. Fixing means 13 may be clamping devices fixedly supporting both ends of an object 11.

A first signal generator 10 may be mounted at a side of the object 11 fixed by clamping devices. A first signal generator 10 may be mounted at a position apart from a side of the object 11 and apply a first excitation ultrasonic wave 10a to the object 11 in a non-contact condition. Applying a first excitation ultrasonic wave 10a to the object 11 using a first signal generator 10 is for identifying a first frequency signal 10b generated by applying the first excitation ultrasonic wave 10a to the object 11.

Now, a case in which a first excitation ultrasonic wave 10a less than or equal to 45 kHz is applied as a low frequency wave will be explained. However, a low frequency range is not limited to frequencies less than or equal to 45 kHz, and it may be changed according to the type of the object 11.

A second signal generator 20 may be mounted at a position near to the first signal generator 10, the position being also apart from the object 11. The second signal generator 20 applies a second excitation ultrasonic wave 20a to the object 11 in a non-contact condition. Applying a second excitation ultrasonic wave 20a to the object 11 using the second signal generator 20 is for identifying a second frequency signal 20b generated by applying the second excitation ultrasonic wave 20a to the object 11.

Now, a case in which a second excitation ultrasonic wave 20a ranging from 190 kHz to 200 kHz is applied as a high frequency wave will be explained. However, a high frequency range is not limited to the range from 190 kHz to 200 kHz, and it may be changed according to the type of the object 11.

The first signal generator 10 and the second signal generator 20 may be selectively controlled by a first controller 30. That is, the first controller 30 may selectively control a sequential operation of the first signal generator 10 and the second signal generator 20 and a simultaneous operation of them.

In more detail, the first controller 30 may perform a first step of applying sequentially the first excitation ultrasonic wave 10a and the second excitation ultrasonic wave 20a to the object 11. As a result, the first frequency signal 10b by the applying of the first excitation ultrasonic wave 10a and the second frequency signal 20b by the applying of the second excitation ultrasonic wave 20a may be independently generated from the object 11.

The first frequency signal 10b and the second frequency signal 20b may be transformed into frequency signals by a signal generator. In addition, the first controller 30 may perform a second step of applying simultaneously the first excitation ultrasonic wave 10a and the second excitation ultrasonic wave 20a to the object 11. Accordingly, synthesized frequency signals 10c and 20c by the simultaneous applying of the first excitation ultrasonic wave 10a and the second excitation ultrasonic wave 20a may be generated from the object 11.

The first frequency signal 10b and the second frequency signal 20b of the first step and the synthesized frequency signals 10c and 20c may be measured by a signal measuring instrument 41 and transmitted to a storing portion 40. The storing portion 40 may store the first frequency signal 10b and the second frequency signal 20b generated from the object 11 by the first step control of the first controller 30. Further, the storing portion 40 may store the synthesized frequency signals 10c and 20c generated from the object 11 by the second step control of the first controller 30.

The first frequency signal 10b, the second frequency signal 20b, and the synthesized frequency signals 10c and 20c stored in the storing portion 40 may be transmitted to a second controller 50. The second controller 50 may receive the first frequency signal 10b, the second frequency signal 20b, and the synthesized frequency signals 10c and 20c from the storing portion 40 and calculate derived frequency signals 12 by removing an overlapping portion of the first frequency signal 10b and the second frequency signal 20b from the synthesized frequency signals 10c and 20c. Further, the second controller 50 may determine whether at least one of the derived frequency signals 12 is larger than a predetermined value or beyond a predetermined range.

The predetermined range of the derived frequency signals 12 may be predetermined with a proper range according to variations of the type of the object 11. In addition, the confirmation of the second controller 50 may be displayed using a display portion 51. The display portion 51 may be installed to receive signals of the second controller 50 such that a worker can check an object 11 for abnormality condition visually.

As described above, the second controller 50 may confirm that damage such as crack has happened in the object 11 if the at least one of the derived frequency signals 12 is larger than a predetermined value or beyond a predetermined range. Further, a failure measure such as rapidly replacing a damaged object can be performed because it is possible to identify damage of the object 11 quickly and precisely.

Figure 3:
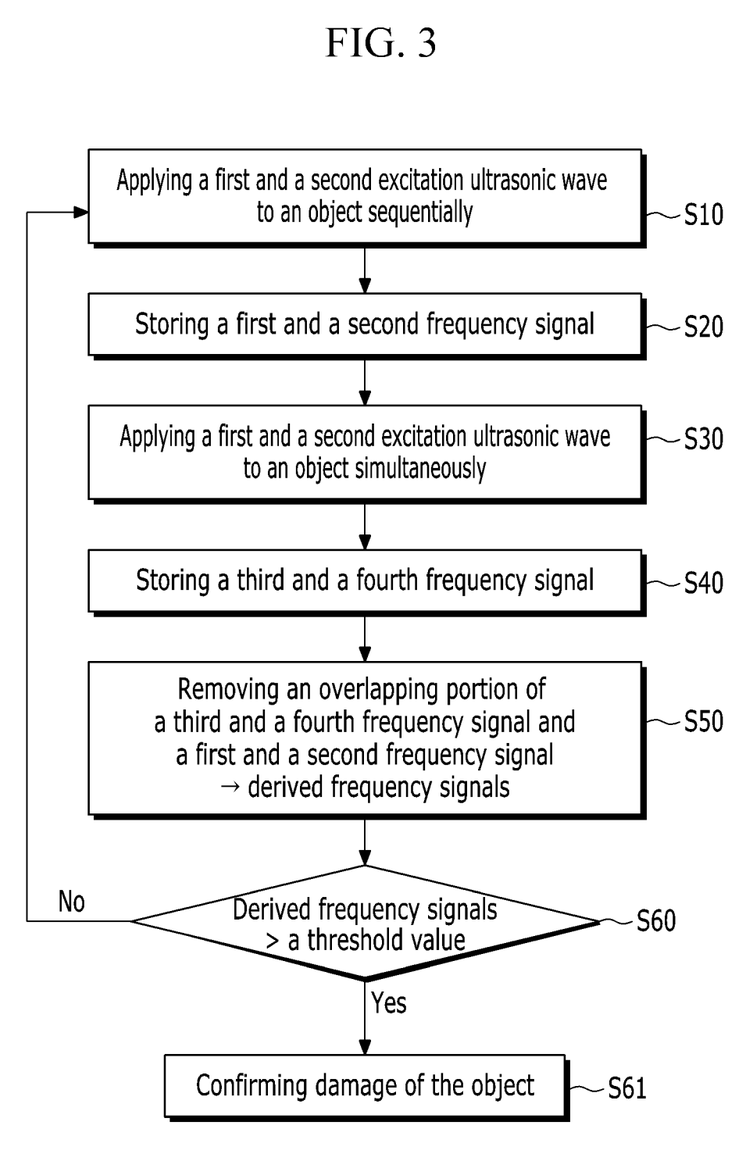
FIG. 3 is a flow chart illustrating schematically an exemplary non-contact durability diagnosis method according to the present disclosure.

FIG. 3 is a flow chart illustrating schematically an exemplary non-contact durability diagnosis method according to the present disclosure.

Same reference numerals as ones in FIG. 1 and FIG. 2 indicate same members having same functions. Hereinafter, the non-contact durability diagnosis method will be explained in detail referring to drawings.

At least two excitation ultrasonic waves may be applied to an object sequentially and non-contactly and frequency signals generated from the object may be stored.

Hereinafter, an exemplary case in which excitation ultrasonic waves are a first excitation ultrasonic wave 10a and a second excitation ultrasonic wave 20a will be explained.

First, a first excitation ultrasonic wave 10a and a second excitation ultrasonic wave 20a having a different frequency from a frequency of a first excitation ultrasonic wave 10a are applied to the object 11 sequentially and non-contactly (S10).

In a step S10, a first excitation ultrasonic wave 10a and a second excitation ultrasonic wave 20a may be applied to an object 11 sequentially with a time interval therebetween. The first excitation ultrasonic wave 10a may be applied by a first signal generator 10 and the second excitation ultrasonic wave 20a may be applied by a second signal generator 20. The first excitation ultrasonic wave 10a and the second excitation ultrasonic wave 20a may be applied to an object 11 selectively according to controlling of a first controller 30.

Hereinafter, a case in which the first excitation ultrasonic wave 10a has a frequency lower than that of the second excitation ultrasonic wave 20a. That is, the first excitation ultrasonic wave 10a has a low frequency and the second excitation ultrasonic wave 20a has a high frequency.

Subsequently, a first frequency signal 10b generated from the object 11 by the first excitation ultrasonic wave 10a of the step S10 and a second frequency signal 20b generated from the object 11 by the second excitation ultrasonic wave 20a may be respectively measured. The first frequency signal 10b and the second frequency signal 20b measured in the step S10 may be stored in a storing portion 40 (S20). In addition, at least two excitation ultrasonic waves may be applied to an object simultaneously and non-contactly and frequency signals generated from the object may be stored.

In this case, an exemplary case in which excitation ultrasonic waves are a first excitation ultrasonic wave 10a and a second excitation ultrasonic wave 20a as described above, will be explained.

A first excitation ultrasonic wave 10a and a second excitation ultrasonic wave 20a are applied to an object 11 simultaneously and non-contactly (S30). In step S30, a first excitation ultrasonic wave 10a and a second excitation ultrasonic wave 20a may be applied to an object 11 simultaneously according to controlling of a first controller 30.

Subsequently, a third frequency signal 10c and a fourth frequency signal 20c generated from the object 11 by the simultaneous applying of the first excitation ultrasonic wave 10a and the second excitation ultrasonic wave 20a in the step S30 may be measured and stored (S40). In step S40, the third frequency signal 10c and the fourth frequency signal 20c may be stored in a storing portion 40.

Next, derived frequency signals remaining after removing an overlapping portion of the frequency signals of the step S40 and the frequency signals of the step S20 from the frequency signals of the step S40 may be stored. That is, derived frequency signals 12 derived by removing an overlapping portion of the third frequency signal 10c and the fourth frequency signal 20c of the step S40 and the first frequency signal 10b and the second frequency signal 20b of the step S20 from the third frequency signal 10c and the fourth frequency signal 20c of the step S40 may be stored (S50).

In a step S50, the derived frequency signals 12 may be stored a storing portion 40.

Figure 4:
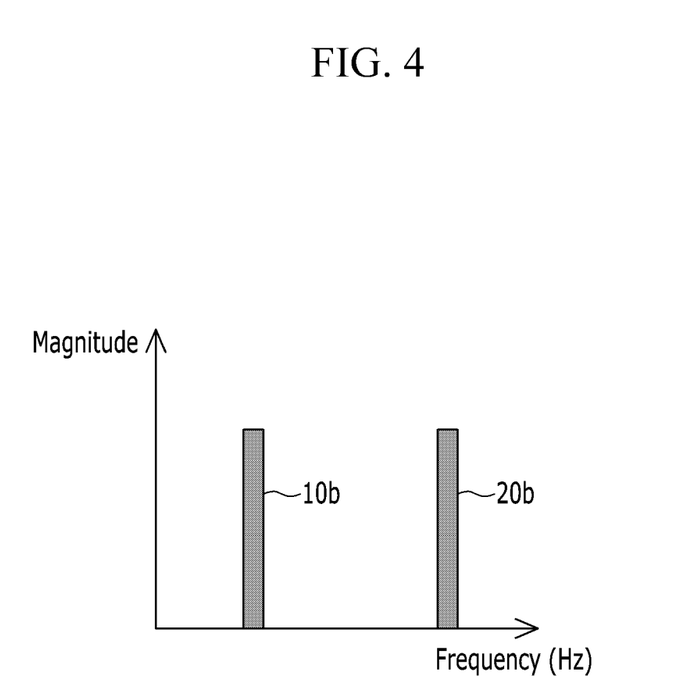
FIG. 4 is a graph drawing illustrating schematically a first frequency signal and a second frequency signal generated by applying sequentially a first excitation ultrasonic wave and a second excitation ultrasonic wave to an object.
Figure 5:
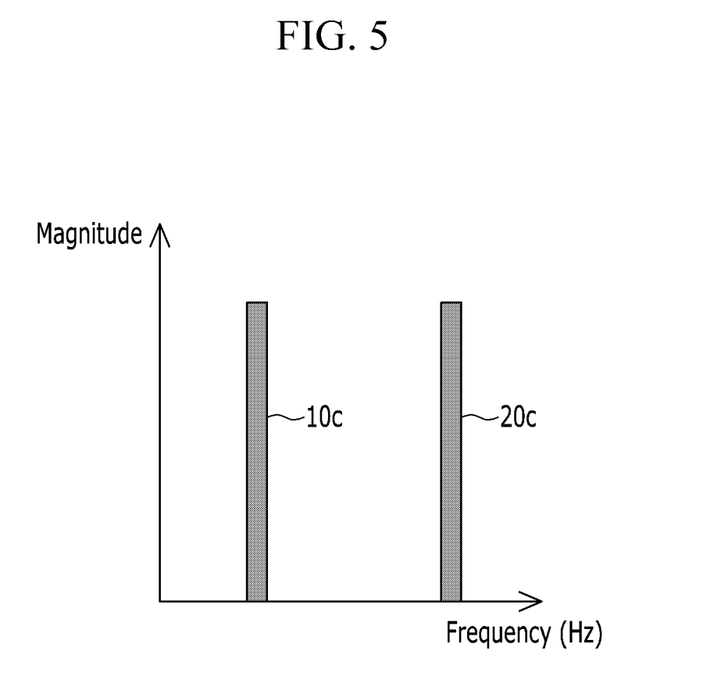
FIG. 5 is a graph drawing illustrating schematically a third frequency signal and a fourth frequency generated by applying simultaneously a first excitation ultrasonic wave and a second excitation ultrasonic wave to an object.
Figure 6:
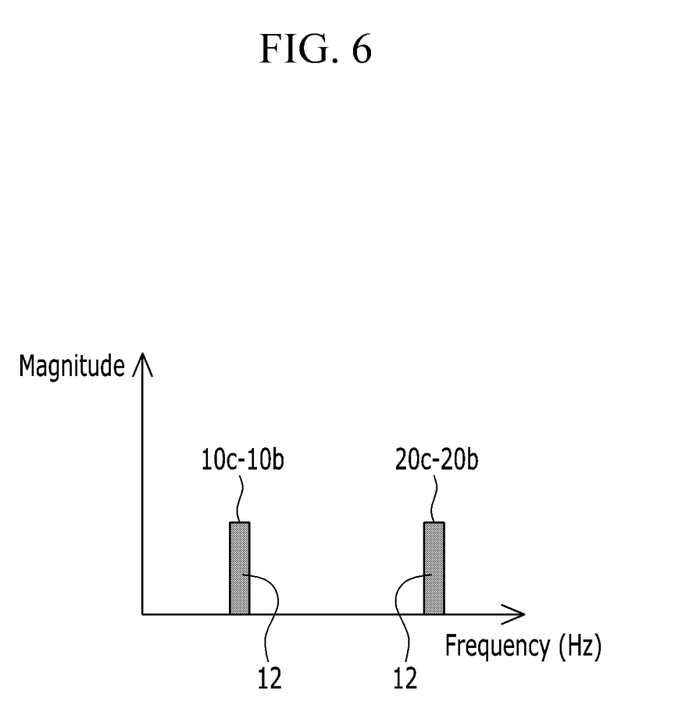
FIG. 6 is a graph drawing acquired by removing an overlapping portion of a first frequency signal and a second frequency signal of FIG. 4 from a third frequency signal and a fourth frequency signal in the graph drawing of FIG. 5.

FIG. 4 is a graph drawing illustrating schematically a first frequency signal and a second frequency signal generated by applying sequentially a first excitation ultrasonic wave and a second excitation ultrasonic wave to an object. FIG. 5 is a graph drawing illustrating schematically a third frequency signal and a fourth frequency generated by applying simultaneously a first excitation ultrasonic wave and a second excitation ultrasonic wave to an object. FIG. 6 is a graph drawing acquired by removing an overlapping portion of a first frequency signal and a second frequency signal of FIG. 4 from a third frequency signal and a fourth frequency signal in the graph drawing of FIG. 5.

As illustrated in FIG. 4 to FIG. 6, the derived frequency signals 12 remain if the first frequency signal 10b and the second frequency signal 20b are respectively removed from the third frequency signal 10c and the fourth frequency signal 20c.

The exemplary non-contact durability diagnosis method may confirm the object 11 is damaged (S61) if at least one of the derived frequency signals 12 of the step S50 is larger than a predetermined threshold value (S60). That is, the method may confirm in the step S61 that the object 11 is damaged if the at least one of the derived frequency signals 12 generated from the object 11 is larger than the threshold value predetermined according to the type of the object 11.

Figure 7:
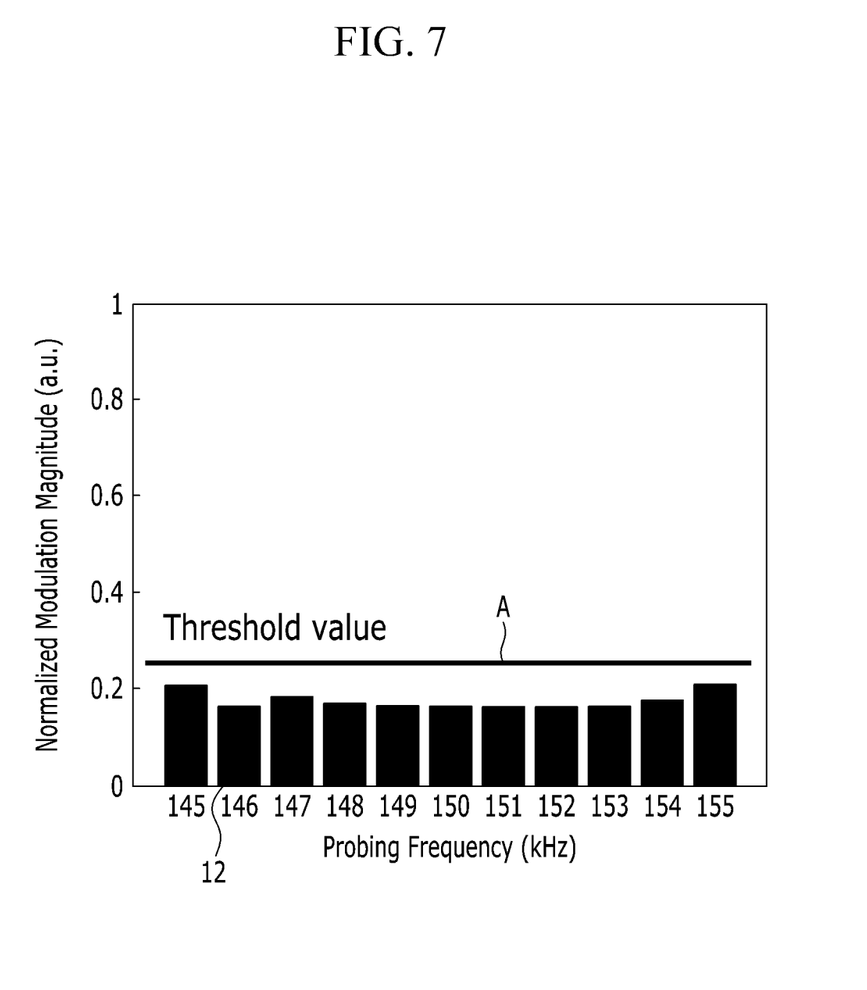
FIG. 7 is a graph drawing illustrating schematically derived frequency signals of a non-damage object.
Figure 8:
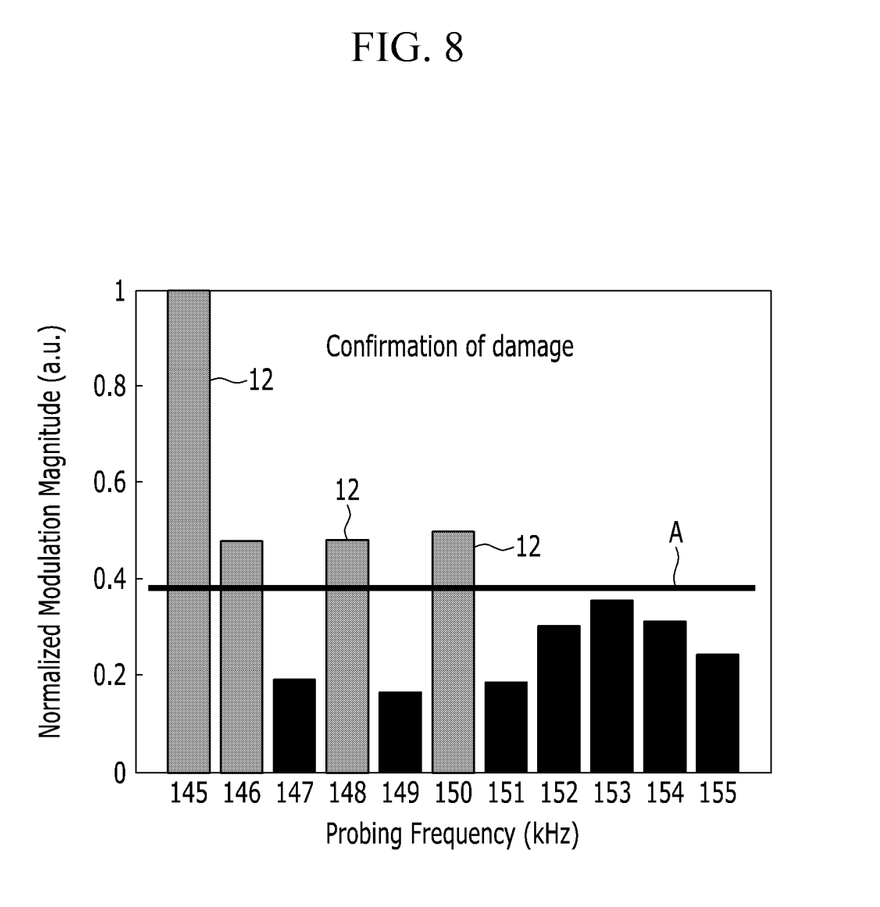
FIG. 8 is a graph drawing illustrating schematically derived frequency signals of a damaged object.

FIG. 7 is a graph drawing illustrating schematically derived frequency signals of a non-damage object. FIG. 8 is a graph drawing illustrating schematically derived frequency signals of a damaged object.

As shown in FIG. 7, derived frequency signals 12 of an undamaged object are not larger than a threshold value A, which is a normal condition of the object. As shown in FIG. 8, derived frequency signals 12 of a damaged object are larger than a threshold value A, which is an abnormal condition. Therefore, if at least one of derived frequency signals 12 is larger than a threshold value A, the method may confirm that an object 11 is damaged. Further, if at least one of derived frequency signals 12 is greater than a predetermined value or beyond a predetermined range, the method may notify the user of damage information of an object 11. The method may indicate damage information and notify the user of the abnormal condition of the object 11 using a display portion 51.

As described above, the method may confirm that damage such as crack has happened in the object 11 if the derived frequency signals 12 are larger than a predetermined range. Therefore, a failure measure such as rapidly replacing a damaged object can be performed because it is possible to identify damage of the object 11 quickly and precisely.

While this disclosure has been described in connection with what is presently considered to be practical embodiments, it is to be understood that the disclosure is not limited to the disclosed embodiments, but, on the contrary, is intended to cover various modifications and equivalent arrangements included within the spirit and scope of the appended claims.

What is claimed is:

1. A non-contact durability diagnosis method comprising:
   (a) applying non-contactly and sequentially a first plurality of excitation ultrasonic waves to an object and storing frequency signals generated from the object;
   (b) applying non-contactly and simultaneously a second plurality of excitation ultrasonic waves to the object and storing frequency signals generated from the object;
   (c) storing derived frequency signals remaining after removing an overlapping portion of the frequency signals of step (a) and the frequency signals of step (b); and
   (d) determining that the object is damaged when at least one of the generated frequency signals of step (c) is larger than a predetermined value.

2. The non-contact durability diagnosis method of claim 1, wherein:
   step (a) further comprises:
   (a-1) applying sequentially a first excitation ultrasonic wave and a second excitation ultrasonic wave having a frequency different than a frequency of the first excitation ultrasonic wave; and
   (a-2) measuring and storing a first frequency signal generated from the object by the first excitation ultrasonic wave and a second frequency signal generated from the object by the second excitation ultrasonic wave.

3. The non-contact durability diagnosis method of claim 2, wherein:
   step (b) further comprises:
   (b-1) applying non-contactly and simultaneously a third excitation ultrasonic wave and a fourth excitation ultrasonic wave to the object, the third and fourth excitation ultrasonic waves having same frequencies with the first and second excitation ultrasonic waves respectively; and
   (b-2) measuring and storing a third frequency signal and a fourth frequency signal generated from the object by the simultaneous application of the third excitation ultrasonic wave and the fourth excitation ultrasonic wave in step (b-1).

4. The non-contact durability diagnosis method of claim 3, wherein
   the stored frequency signals in step (c) are derived by removing an overlapping portion of the first frequency signal and the second frequency signal of step (a-2) and the third frequency signal and the fourth frequency signal of step (b-2) step from the third frequency signal and the fourth frequency signal of step (b-2).

5. The non-contact durability diagnosis method of claim 2, wherein the first excitation ultrasonic wave has a frequency lower than that of the second excitation ultrasonic wave.

6. The non-contact durability diagnosis method of claim 1, further comprising:
   (e) notifying a user of damage information of the object when at least one of the derived frequency signals is greater than a predetermined value.

7. The non-contact durability diagnosis method of claim 6, further comprising:
   (f) displaying the damage information on a display portion.

8. A non-contact durability diagnosis apparatus comprising:
   a first signal generator non-contactly applying an excitation ultrasonic wave of a first frequency to an object and generating a frequency signal from the object;
   a second signal generator non-contactly applying an excitation ultrasonic wave of a second frequency different than the first frequency to the object and generating another frequency signal from the object;
   a first controller controlling the first signal generator and the second signal generator in order to sequentially perform a first step of generating first and second frequency signals from the object by applying A first excitation ultrasonic wave of the first frequency and a second excitation ultrasonic wave of the second frequency sequentially to the object and a second step of generating synthesized frequency signals from the object by applying a third excitation ultrasonic wave of the first frequency and a fourth excitation ultrasonic wave of the second frequency simultaneously to the object;
   a storing portion storing the first frequency signal and the second frequency signal generated from the object by the first step and the synthesized frequency signals generated from the object by the second step; and
   a second controller identifying frequency signals derived by removing an overlapping portion of the first frequency signal and the second frequency signal, from the synthesized frequency signals, and determining that the object is damaged if at least one of the derived frequency signals is larger than a predetermined range or value.

9. The non-contact durability diagnosis apparatus of claim 8, wherein the first frequency is lower than the second frequency.

10. The non-contact durability diagnosis apparatus of claim 8, further comprising:
a display portion connected to the second controller and displaying damage information of the object.

* * * * *